United States Patent [19]

Rivetti et al.

[11] Patent Number: 4,659,845
[45] Date of Patent: Apr. 21, 1987

[54] PROCESS FOR THE PRODUCTION OF N-METHYLCARBAMATES

[75] Inventors: Franco Rivetti, Schio; Franco Mizia; Guido Garone, both of Milan; Ugo Romano, Vimercate, all of Italy

[73] Assignee: Enichem Sintesi S.p.A., Palermo, Italy

[21] Appl. No.: 731,538

[22] Filed: May 7, 1985

[30] Foreign Application Priority Data

Feb. 8, 1985 [IT] Italy ............................... 19453 A/85

[51] Int. Cl.$^4$ ................. C07D 317/44; C07C 125/067
[52] U.S. Cl. .................................... 549/438; 549/452; 549/467; 560/132; 560/134; 560/135; 560/136; 560/345
[58] Field of Search ................ 549/438, 452, 467; 560/132, 134, 135, 136, 345

[56] References Cited

U.S. PATENT DOCUMENTS 4,097,676  6/1978  Romano ............................. 560/132
4,123,450 10/1978  Weber, Jr. ......................... 260/453 P
4,195,031  3/1980  Reichmann et al. ................. 560/345

*Primary Examiner*—Dolph H. Torrence
*Attorney, Agent, or Firm*—Hedman, Gibson, Costigan & Hoare

[57] ABSTRACT

Process for the production of N-methylcarbamates:

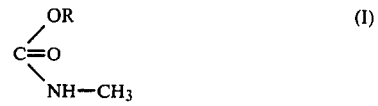

(wherein RO- is the radical of a substituted phenol or of a naphthol), wherein:

in a first reaction step methylamine and diphenyl carbonate are reacted with each other, operating in the liquid phase and as a continuous process, in order to form phenol and phenyl-N-methylurethane;

in a second reaction step phenyl-N-methylurethane, within the related reaction mixture outcoming from the first step, is thermally continuously decomposed, to yield a gaseous stream containing methyl isocyanate, from which the components different than methyl isocyanate are condensed off;

in a third step the methyl isocyanate stream, outcoming from the second step, after an optional preliminary condensation, is continuously fed and contacted with a solution of a substituted phenol or of a naphthol in an inert organic solvent, containing a basic catalyst, to form N-methylcarbamate (I);

N-methylcarbamate (I) is finally recovered from the reaction mixture outcoming from the third step.

18 Claims, 1 Drawing Figure

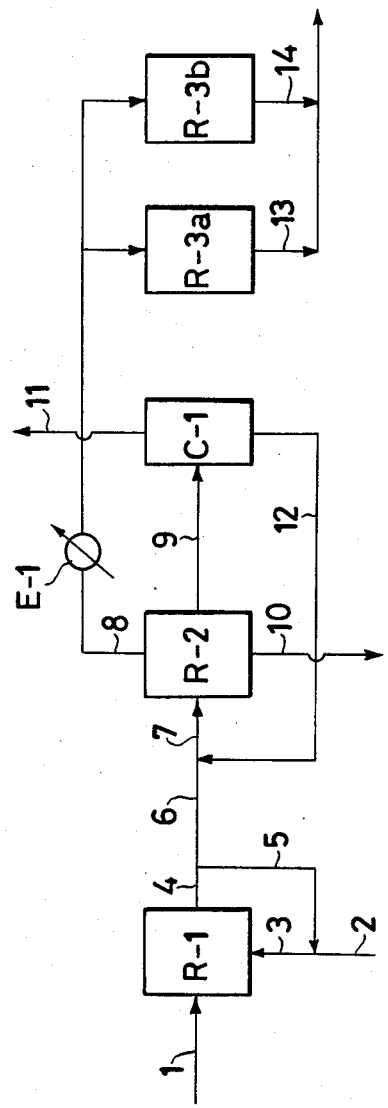

PROCESS FOR THE PRODUCTION OF N-METHYLCARBAMATES

The present invention relates to an improved process for the production of N-methylcarbamates, such process being of the continuous type.

N-methylcarbamates are valuable products, many of which are known to have activity as drugs for phytopharmacological use, such as e.g. 2,3-dihydro-2,2-dimethylbenzofuran-7-yl-N-methylcarbamate (known as CARBOFURAN), 1-Naphthyl-N-methylcarbamate (known as CARBARYL) and 2-isopropoxyphenyl-N-methylcarbamate (known as PROPOXUR) is known.

N-Methylcarbamates are obtained, according to the known art, by reacting methyl isocyanate with a substituted phenol or with a naphthol, operating in an inert organic solvent, and in the presence of a basic catalyst. Reference is made to this regard to R. J. Kuhr and H. W. Dorough "Carbamate Insecticides; Chemistry, Biochemistry and Toxicology", CRC Press (1977).

The main drawback of N-methyl carbamate preparation processes resides in the use of such a reactant as methyl isocyanate, which is highly toxic and dangerous during the delivery and storage steps.

Methyl isocyanate is indeed very volatile (boiling point 38° C.) and polymerizes easily, with an hexothermic reaction course, in bulk in the liquid state.

When traces of acids, bases or metals are present, the polymerization can occur in an explosive way. Finally, methyl isocyanate can undergo violent hydrolysis reactions with water, characterized by a pressure surge (formation of carbon dioxide) and by a high inflammability.

From the foregoing it appears desirable that a process for the production of N-methylcarbamates be available, not requiring the storage of methyl isocyanate and wherein the amount of free methyl isocyanate involved be small at each time.

According to European Patent Application Publication No. 80.584, alkyl isocyanates are obtained, by means of the decomposition of phenyl-N-alkylurethanes by operating in the presence of phenol.

According to U.S. Pat. No. 4,097,676 phenyl-N-alkylurethanes are prepared by means of the reaction of diphenyl carbonate with an alkylamine. In the experimental examples of U.S. Pat. No. 4,097,676 the reaction of diphenyl carbonate with alkylamine is carried out in an inert organic solvent such as benzene and dioxane.

It has been now found that the reaction disclosed in U.S. Pat. No. 4,097,676 takes place favourably up to a practically complete conversion of reactants, when it is carried out as a continuous process, using as the liquid reaction medium the same diphenyl carbonate/alkylamine reaction mixture.

It has been moreover found that the decomposition reaction of phenyl-N-alkylurethanes of European Patent Application Publication No. 80.584 can be carried out as a continuous process, directly on the mixture outcoming from the reaction between diphenyl carbonate and alkylamine.

Moreover, when said decomposition reaction of phenyl-N-alkylurethanes is carried out at an only partial conversion per passage, and hence with the recycle of unreacted product, the development of alkyl isocyanate is constant and regular, so as to make it possible a continuous or semi-continuous running of the subsequent reaction with a substituted phenol or with a naphthol.

On such a background, the present invention relates to the preparation of N-methylcarbamates:

(wherein RO— is a radical of a substituted phenol or of a naphthol) by means of a process comprising the following sequential steps:

1st step—To a first reactor diphenyl carbonate and methylamine are continuously fed, together with a recycled liquid stream constituted by the reaction mixture discharged from said 1st reactor and the reaction is carried out in the liquid phase, with a feed molar ratio of methylamine to diphenyl carbonate of from 0.8/1 to about 1/1 and at a temperature of from 20° C. to 80° C., in order to form phenyl-N-methylurethane and phenol;

2nd step—To a second reactor the reaction mixture outcoming from the first step and a recycled liquid stream containing phenyl N-methylurethane are continuously fed, operating in boiling liquid phase, at a temperature of from 180° to 220° C. and under a pressure of from 200 mmHg to the atmospheric pressure, in order to partly decompose phenyl-N-methylurethane into phenol and methyl isocyanate and to develop a gaseous stream containing phenol, methyl isocyanate and unchanged phenyl-N-methylurethane, said gaseous stream being submitted to partial condensation, in order to separate a gaseous stream of methyl isocyanate from a liquid stream of phenol and phenyl-N-methylurethane, this latter being in its turn submitted to treatments for the separation and recycle of phenyl-N-methylurethane;

3rd step—To a third reactor the methyl isocyanate stream, outcoming from the second step is continuously fed and is contacted, possibly after having been condensed, with a solution of a substituted phenol or of a naphthol in an inert organic solvent, operating at a temperature of from 0° to 50° C., in the presence of a basic catalyst to form N-methylcarbamate (I); N-methylcarbamate is finally recovered from the reaction mixture outcoming from the third step.

1st Step

In the first step of the process of the present invention, diphenyl carbonate and methylamine are reacted with each other to yield phenyl-N-methylurethane and phenol according to the reaction scheme:

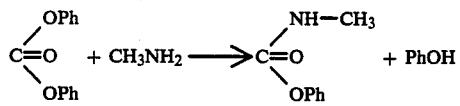

(wherein Ph is the phenyl radical)

The feed molar ratio of methylamine to diphenyl carbonate may generally vary from 0.8/1 to about 1/1. It is very desirable however to use a molar ratio of 1/1 or at least very close to that value.

The reaction temperature is conveniently held at values comprised within the range of from 20° to 80° C. Temperatures lower than 20° C. may be used, but with the disadvantage of a too low reaction speed. On the other hand, temperatures higher than 80° C. are undesired, in that they favour the occurrence of a secondary reaction leading to the formation of N,N'-dimethylurea, according to the following reaction scheme:

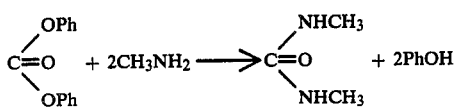

(wherein Ph is the phenyl radical)

This reaction occurs to a noticeable extent especially over about 100° C.

The pressures under which the reaction is carried out may vary from room pressure to about 5 bar. Generally, the reaction is carried out under the autogenous pressure of the system at the selected temperature.

The reaction medium is constituted by the same reaction mixture, which is conveniently recycled to the first step reactor.

In practice, to the first step reactor a continuous stream of methylamine and a continuous stream of diphenyl carbonate dissolved in the recycled liquid mixture may be fed. For convenience, in this latter stream the concentration of diphenyl carbonate may vary from 5 to 60% by weight, in that within this concentration range homogenous liquid streams are obtained, with a low viscosity value within the temperature range within which the reaction is carried out, an easy handling of such streams being thus possible.

The first step reactor may be a stirred reactor, into which the reactants and the recycled liquid medium are continuously fed, and from which the reaction mixture is continuously discharged. As an alternative, a long-shaped reactor, e.g. a tubular reactor may be used, at an end of which the reactant and the recycled liquid medium are continuously fed, and at the other and of which the reaction mixture is discharged.

By operating within the previously described conditions, the reaction is completed or substantially completed, in a time of from 15 to 60 minutes, in the absence of substances having a catalytic effect on the same reaction.

In particular, by operating under the previously indicated conditions and with stoichiometric or nearly stoichiometric amounts of the reactants, the conversion of diphenyl carbonate is typically greater than about 98%, with a selectivity for phenyl-N-methylurethane typically greater than 99% relative to the converted diphenyl carbonate, all percentages being on molar basis.

The reaction mixture discharged from the first step reactor is partly recycled, as previoulsy indicated, and the residual amount is continuously sent to the second step reactor.

2nd Step

In the second step of the present invention, phenyl-N-methylurethane is thermally decomposed into methyl isocyanate and phenol according to the following reaction scheme:

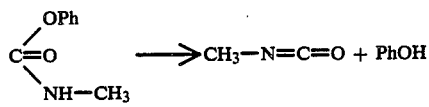

(wherein Ph is the phenyl radical).

More particularly, according to the process of the present invention, to the second step reactor the liquid stream constituted by the reaction products of the first step and a recycled liquid phenyl-N-methylurethane stream are continuously fed, and the reaction is carried out in boiling liquid phase, at a temperature of from 180° to 220° C., under a pressure of from 200 mmHg up to the atmospheric pressure, in the absence of substances having catalytic action on the decomposition reaction, in order to partly (10–90%) decompose phenyl-N-methylurethane into phenol and methyl isocyanate. Under these conditions, in the second step reactor a gaseous stream containing methyl isocyanate, phenol and unconverted phenyl-N-methylurethane is developed. This stream is cooled, e.g. at a temperature of the order of 80°–100° C., in order to separate a gaseous stream of methyl isocyanate from a liquid stream of phenol and phenyl N-methylurethane. The liquid stream so obtained is distilled in order to partly or totally separate the phenol as the head product, from a tail product formed by or containing phenyl-N-methylurethane, and this tail product is recycled to the second step reactor as previously indicated.

In the preferred practical embodiment the process in the second step is carried out at a temperature of the order of 210° C., under atmospheric pressure or under a pressure close to the atmospheric, with an average residence time (calculated as the ratio of the volumetric feed flow rate to the free volume of the reactor) of from 0.5 to 3 hours. Moreover, to the reactor enough heat is supplied to generate a flow rate (on a weight basis) of evaporated matter from 1.5 to 11 times as large as the feeding flow rate. Under these conditions, conversions per passage of phenyl-N-methylurethane are accomplished of from 65 to about 85% relative to the feeding amount, and in the reactor a gaseous stream is generated, containing from about 9 to about 22% by weight of unconverted phenyl N-methylurethane, from 63 to about 71% by weight of phenol and from about 15 to about 20% by weight of methyl isocyanate.

This gaseous stream is cooled to a temperature of from 80° to 100° C. in order to separate a condensate constituted by phenol and phenyl-N-methylurethane from a gaseous stream of methyl isocyanate, which is sent to the third step. The condensate is partly recycled to the second step reactor (recycle ratio of from about 0.5 to about 10) and the residual portion is sent to a distillation column operated under a pressure, measured at the top, of the order of 10 mmHg, with a top temperature of 77°–80° C. and with a bottom temperature of from 100° to 110° C. Under these conditions at the top of the column a head stream of phenol is separated, which is recovered, and at the bottom a liquid stream is obtained containing phenol and phenyl-N-methylurethane, in nearly equimolecular proportions, which is recycled.

The reactor within which the second step is carried out is preferably a stirred reactor, atop of which a partial condenser is assembled, preceded or not preceded by some distillation plates or by a packed length.

By operating under the preferred conditions previously disclosed, a complete or nearly complete conversion of phenyl-N-methylurethane is obtained, with a selectivity for methyl isocyanate typically higher than 98% by mole.

3rd Step

In the third step of the process according to the present invention, methyl isocyanate outcoming as gaseous stream from the second step, is reacted, possibly after having been condensed, with a substituted phenol or with a naphthol dissolved in an organic solvent, according to the following reaction scheme:

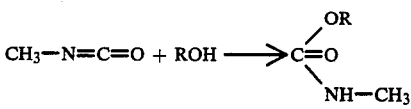

wherein RO— represents the radical of a substituted phenol or of a naphthol.

Example of ROH compounds useful to the purposes of the present invention are:

phenol sustituted with from one to three substituent groups, equal or different to each other, selected among alkyl, oxyalkyl, thioalkyl, aminoalkyl, alkylene-oxyalkyl, alkylene-thio-alkyl and alkylene-aminoalkyl groups wherein the alkyl group, straight or branched, contains from 1 to 5 carbon atoms (preferably from 1 to 3 carbon atoms) and the alkylene group contains 1 or 2 carbon atoms (it is preferably methylene);
1-naphthol;
2-naphthol;
2,3-dihydro-2,2-dimethylbenzofuran-7-ol;
2,2-dimethyl-1,3-benzodioxol-4-ol;
2-(1,3-dioxolan-2-yl)-phenol;

Examples of ROH compounds preferred to the purposes of the present invention are:
3,5-xylenol;
3,4-xylenol;
2-isopropylphenol;
2-isopropoxyphenol;
2-(ethylthiomethyl)-phenol;
2-cresol;
3-isopropyl-5-methylphenol;
4-methylthio-3,5-dimethylphenol;
4-dimethylamino-3-methylphenol;
1-naphthol;
2,3-dihydro-2,2-dimethylbenzofuran-2-ol; and
2,2-dimethyl-1,3-benzodioxol-4-ol.

According to the process of the present invention, methyl isocyanate, outcoming from the second step, after its possible condensation, is continuously fed and contacted with a solution of the ROH compound in an inert organic solvent, containing also a basic catalyst.

Organic solvents suitable to this purpose are aromatic hydrocarbons, such as benzene, toluene, xylene and cumene; ketones such as acetone, methylethylketone and methylisobutylketone; esters such as ethyl acetate, methyl acetate, dimethyl carbonate and diethyl carbonate; chlorinated aliphatic hydrocarbons such as chloroform, methylene chloride, carbon tetrachloride and dichloroethane; ethers such as diethyl ether and tetrahydrofuran.

Generally, the concentration of the compound in the related solution in the organic solvent varies from 5 to 60% by weight.

As catalysts for the third step reaction substances of basic character are used such as tertiary amines, heterocyclic bases, alkoxides and carbonates of alkali or alkali-earth metals, or organic derivatives of such metals as tin and titanium. Specific examples of catalysts useful to this purpose are triethylamine, diisopropylethylamine, pyridine, 4-dimethylaminopyridine, N-methylimidazole, sodium methoxide, sodium ethoxide, sodium carbonate, dibutyltin dilaurate, dibutyltin diacetate and titanium isopropoxide.

Preferred catalysts are the tertiary amines and tin organic compounds.

The amount of catalyst used for the third step reaction may generally vary from 0.001 to 0.1 moles per each mole of ROH compound.

The reaction temperatures are not particularly critical, but the reaction is preferably carried out within a temperature range of from 0° to 50° C.

The reaction is preferably carried out under the atmospheric pressure, or however with no imposed overpressure.

In the third step the reaction is moreover carried out with an equimolar or nearly equimolar ratio between ROH compound and methyl isocyanate, and in particular with ratios of from 1/1 to 1.1/1.

The third step of the process according to the present invention may be carried out by using a plurality of reactors in parallel arrangement, each containing the solution of ROH compound in the selected organic solvent besides the catalyst. In this case, the stream of methyl isocyanate, possibly after having been liquified, is continuously fed to the first reactor, until the desired molar ratio between the reactants is reached; the methyl isocyanate stream is then diverted to the second reactor.

At the end of the feeding of methyl isocyanate, the first reactor is maintained under the reaction conditions for a time of the order of 0.5–8 hours, for the purpose of completing the reaction, and N-methylcarbamate is finally recovered from the reaction mixture.

The cycle is repeated for the second reactor, and so on.

According to another practical embodiment of the present invention, the stream of methyl isocyanate outcoming from the second step, possibly liquified, and a stream constituted by the solution of ROH compound in the selected organic solvent and containing also the catalyst, are continuoulsy fed to a third step reactor wherein the reaction is carried out under the hereinabove disclosed general conditions, and with a residence time which may generally vary from 0.5 to 8 hours. From the reactor the reaction mixture is continuously discharged, which is submitted to the suitable treatments to separate N-methylcarbamate.

The third step is preferably conducted within stirred reactors in the embodiment with more reactors in parallel array. In the continuous embodiment, a set of continuous reactors placed in series is preferably used, or a reactor of a long tubular shape is used, to an end of which the reactants are continuously fed, and from whose other end the reaction mixture is continuously discharged.

By operating within the range of conditions previously described, typically N-methylcarbamate is obtained, with a yield typically greater than 98% molar with reference to the reactants fed. N-Methylcarbamate is separated from the reaction mixture outcoming from the third step by any known techniques, such as concentration, crystallization, filtration, drying or any combination thereof. In the preferred embodiment, the solvent for the third step is so selected, as to favour the precipitation of N-methylcarbamate, so as to facilitate the separation thereof from the reaction mixture, which can hence be directly recycled, after the preliminary dissolving of the ROH compound. If necessary, or desired, so separated N-methylcarbamate may be purified, e.g. by crystallization from an inert solvent, by dissolving it at high temperatures in a suitable solvent and causing then the precipitation thereof by cooling its solution. Conveniently, the temperature at which raw N-methylcarbamate solution is heated will be kept at a lower value than that causing degradation phenomena of such compound, and shall be generally lower than 100° C.

By means of the process of the present invention, N-methylcarbamates are prepared by means of a process in which, at any time, the amount of free methyl isocyanate is kept at extremely low values, overcoming or at least strongly simplifying the problems involved by the use of such a compound. Moreover, the process according to the present invention allows N-methylcarbamates to be prepared with high yields and selectivity, in a simple and cheap way. Moreover, running the process continuously as hereinabove disclosed shows, relative to the batchwise running, the advantages are a greater productivity per equipment volume unit, a greater evenness of the characteristics of the end products, and a greater possibility of process automation.

At last, the process according to the present invention allows an outstanding flexibility to be achieved, in that it makes it possible to produce a wide range of N-methylcarbamates.

The following experimental Examples are illustrative and not limitative of the present invention.

EXAMPLE 1

Referring to the Fig., with R-1 the first step reactor is shown, provided with stirrer and operating at the temperature of 50° C. and under the relative pressure of 1 bar. To a reactor R-1 is continuously fed through the line 1, a stream of 1.3 kg/hour (42 mol/h) of methylamine, and through the line 3 a liquid stream of 22.5 kg/h containing 40% by weight of diphenyl carbonate. The stream of the line 3 is obtained by feeding 9.0 kg/h (42 mol/h) of diphenyl carbonate through the line 2 and 13.5 kg/h of the effluent from the reactor R-1, through the line 5. The residence time in the reactor R-1 is of 0.5 hours and through the line 4 a stream of 23.8 kg/h is discharged, having the following composition: phenol 38% by weight, phenyl N-methylurethane 61% by weight and diphenyl carbonate 0.8% by weight.

This stream is partly (13.5 kg/h) recycled to the reactor R-1 through the line 5 and the balance (10.3 kg/h) constitutes the stream of the line 6 which is delivered to the second step reactor R-2, together with the stream outcoming from the bottom of the column C-1, through the line 12.

In particular, said bottom stream of colum C-1 has a flow rate of 2.3 kg/h, and the following composition: phenol 39% by weight and phenyl-N-methylurethane 61% by weight. Therefore, the resulting stream fed to the reactor R-2 through the line 7, has a flow rate of 12.6 kg/h and the following composition: phenol 38% by weight, phenyl-N-methylcarbamate 61% by weight and diphenyl carbonate 0.7% by weight.

The operating conditions in the second step reactor R-2 are: temperature 210° C., atmospheric pressure and residence time 2 hours. Under these conditions the pyrolysis occurs of phenyl-N-methylurethane and a gaseous stream develops, which is cooled to about 100° C. with consequent partial condensation and obtainment of a liquid phase having the following composition: phenol 86.2% by weight and phenyl-N-methylurethane 13.8% by weight. This liquid phase is partly recycled to the second step reactor R-2 (recycle ratio 10) and the balance constitutes the stream of the line 9 which is sent, with a flow rate of 10.1 kg/hour to the distillation column C-1.

The distillation column C-1 operates under a pressure measured at its top of 10 mmHg, at a top temperature of 78° C. and at a bottom temperature of 108° C. Under these conditions at the top of column C-1 phenol is separated at the rate of 7.8 kg/h, and at the bottom of the column of nearly equimolar stream of phenol and phenyl-N-methylurethane (respectively at 39% by weight and 61% by weight) is separated, which is recycled to the pyrolysis reactor R-2, through the line 12, at a flow rate of 2.3 kg/hour.

From the bottom of the pyrolysis reactor R-2 a drainage is periodically effected, through the line 10, in order to eliminate the residual diphenyl carbonate and the high-boiling byproducts which are formed in very small amounts (less than 0.03 kg/h).

The methyl isocyanate which is formed in the pyrolysis in the second step reactor R-2 does not liquify at the temperature at which the partial condensation of pyrolysis products is carried out, and is discharged through the line 8, at a rate of 2.35 kg/h. This stream is liquified in the heat exchanger E-1 and is sent to the reactor R-3a, into which have been previously charged:
2,3-dihydro-2,2-dimethyl-7-benzofuranol: 28.6 kg;
toluene: 86 kg;
triethylamin: 0.18 kg (catalyst).

The methyl isocyanate stream is fed to the reactor R-3a over 4 hours operating at 15° C. and under atmospheric pressure. After this time period, the stream of methyl isocyanate is diverted into the reactor R-3b, operating in parallel with the reactor R-3a and containing the same initial charge of this latter.

After the end of the feeding of methyl isocyanate into the reactor R-3a, the contents of the reactor are kept under stirring at the temperature above indicated, for further 2 hours. The contents of the reactor R-3a are then discharged through the line 13 and are filtered in order to separate precipitated 2,3-dihydro-2,2-dimethyl-benzofuran-7-yl-N-methylcarbamate, which is washed with toluene and dried at 80° C. under 10 mmHg.

The mother liquors containing the excess 2,3-dihydro-2,2-dimethyl-7-benzofuranol, dissolved 2,3-dihydro-2,2-dimethylbenzofuran-7-yl-N-methylcarbamate (1-2% by weight) and the catalyst may be totally recovered (or with a preliminary drainage of a small entity) for the preparation of the solution to be charged to the third step reactors.

An overall amount of 36.0 kg of 2,3-dihydro-2,2-dimethylbenzofuran-7-yl-N-methylcarbamate (CARBOFURAN) is thus obtained, with a yield of 1 kg of valuable product per each kg of diphenyl carbonate (96.8% molar).

The cycle is repeated with the reactor R-3b, results very similar to those of reactor R-3a being obtained.

EXAMPLE 2

The process is carried out as in Example 1, charging into the third step reactors:
1-naphthol: 25.1 kg;
toluene: 75 kg;
triethylamine: 0.18 kg (catalyst).

In one cycle 32.5 kg of 1 naphthyl-N-methylcarbamate (CARBARYL) are obtained, with a yield of 96% molar relative to diphenyl carbonate.

EXAMPLE 3

The process is carried out as in Example 1, charging into the third step reactors:
2-isopropoxyphenol: 26.5 kg;
toluene: 80 kg;
triethylamine: 0.18 kg (catalyst)

In one cycle 34 kg of 2-isopropoxyphenyl-N-methylcarbamate (PROPOXUR) are obtained, with a yield of 97% molar relative to diphenyl carbonate.

EXAMPLE 4

By operating as in Example 1 and charging into the third step reactors are the following compounds:
4-dimethylamino-3-methylphenol;
3,5-xylenol;
3,4-xylenol;
2,2-dimethyl-1,3-benzodioxol-4-ol;
4-methylthio-3,5-dimethylphenol;
3-isopropyl-5-methylphenol;
2-cresol;
2-isopropylphenol; and
2-(ethyl-thiomethyl)-phenol,
the following carbamates can be respectively obtained:
4-dimethylamino-3-methylphenyl-N-methylcarbamate (AMINOCARB);
3,5-xylyl-N-methylcarbamate (XMMC);
3,4-xylyl-N-methylcarbamate (MPMC);
2,2-dimethyl-1,3benzodioxol-4-yl-methylcarbamate (BENDIOCARB);
4-methylthio-3,5-xylyl-N-methylcarbamate (METHIOCARB);
3-isopropyl-5-methyl-N-methylcarbamate (PROMECARB);
2-tolyl-N-methylcarbamate (MTMC)
2-isopropylphenyl-N-methylcarbamate (ISOPROCARB); and
2-(ethyl-thiomethyl)-phenyl-N-methylcarbamate (ETHIOFENCARB).

What is claimed is:

1. In a process for the preparation of N-methylcarbamates having the formula

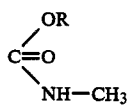

$$\begin{array}{c} \quad\quad OR \\ \quad\quad / \\ C=O \\ \quad\quad \backslash \\ \quad\quad NH-CH_3 \end{array} \quad (I)$$

wherein RO— is a naphthol or substituted phenol radical, wherein diphenyl carbonate reacts with methylamine to form phenyl-N-methylurethane, phenyl-N-methylurethane is thermally decomposed to form methyl isocyanate and the methyl isocyanate is reacted with a substituted phenol or a naphthol to form the N-methylcarbamate (I), the improvement comprising:

(a) feeding streams of diphenyl carbonate and methylamine in a molar ratio of from 0.8-1:1 to a first reaction space with a first recycle mixture discharged from the first reaction space and containing phenyl-N-methylurethane, phenol and unreacted diphenyl carbonate;

(b) reacting diphenyl carbonate and methylamine and the first recycle mixture as a liquid phase at a temperature of from 20° C. to 80° C. in the absence of an organic solvent to form a first reaction product containing phenyl-N-methylurethane, phenol and unreacted diphenyl carbonate;

(c) feeding to a second reaction space streams of the first reaction product and a second recycle mixture discharged from a third reaction space, the second recycle mixture containing phenyl-N-methylurethane and phenol;

(d) reacting the streams of the first reaction product and the second recycle mixture in a liquid phase at a temperature of from 180° C. to 220° C. at a pressure of from 200 mmHg to atmospheric pressure in the absence of an organic solvent to partially decompose phenyl-N-methylurethane and thereby obtain a second reaction product containing unreacted phenyl-N-methylurethane and methyl isocyanate;

(e) forwarding the phenol and unreacted phenyl-N-methylurethane to a third reaction space;

(f) distilling phenol and unreacted phenyl-N-methylurethane in the third reaction space to thereby obtain phenol and the second recycle mixture;

(g) feeding methyl isocyanate formed in the second reaction space to a fourth reaction space;

(h) reacting methyl isocyanate with substituted phenol or naphthol in the fourth reaction space in the presence of an inert organic solvent and a basic catalyst at a temperature of from 0° to 50° C. to thereby obtain N-methylcarbamate.

2. The process of claim 1 further comprising condensing methyl isocyanate prior to reacting the methyl isocyanate in the fourth reaction space.

3. The process of claim 1 wherein the molar ratio of methylamine and diphenyl carbonate is at or about 1:1, and wherein step (a) further comprises combining the stream of the first recycle mixture and the stream of diphenyl carbonate prior to entry into the first reaction space, the combined stream containing from 5 to 60% by weight of diphenyl carbonate.

4. The process of claim 3 wherein step (b) is conducted for 15 to 60 minutes.

5. The process of claim 1 wherein step (d) further comprises (i) decomposing from about 65 to about 85% by weight of phenyl-N-methylurethane supplied to the second reaction space to thereby obtain a gaseous stream containing from about 9 to about 22% by weight of unreacted phenyl-N-methylurethane, (ii) cooling the gaseous stream to thereby separate methyl isocyanate as a gas phase and phenol and phenyl-N-methylurethane as a liquid phase, (iii) separating the liquid phase into the second recycle mixture and the second reaction product, the second recycle mixture being present in an amount of 0.5 to 10 times the amount of the second reaction product.

6. The process of claim 5 wherein step (d) is conducted at a temperature of about 210° C. under atmospheric pressure for 0.5 to 3 hours.

7. The process of claim 5 wherein the step of cooling the gaseous stream is conducted at a temperature of from about 80° to 100° C.

8. The process of claim 1 wherein the second recycle mixture contains about an equimolar amount of each of phenol and phenyl-N-methylurethane.

9. The process of claim 1, wherein the substituted phenol has from one to three substituents, which may be the same or different, and are selected from alkyl, oxyalkyl, thioalkyl, aminoalkyl, alkyleneoxyalkyl, alkylenethioalkyl and alkyleneaminoalkyl, wherein the alkyl group of the substituents has a straight or branched chain and has from 1 to 5 carbon atoms, and the alkylene group of the substituents has 1 or 2 carbon atoms.

10. The process of claim 9 wherein the alkyl group has 1 to 3 carbon atoms and the alkylene group is methylene.

11. The process of claim 1, wherein methyl isocyanate reacts with a compound selected from 3,5-xylenol, 3,4-xylenol, 2-isopropylphenol, 2-isopropoxyphenol, 2-(ethylthiomethyl)-phenol, 2-cresol, 3-isopropyl-5-methylphenol, 4-methylthio-3,5-dimethylphenol, 4-dimethylamino-3-methylphenol, 1-naphthol, 2,3-dihydro-2,2-dimethyl-benzofuran-7-ol, and 2,2-dimethyl-1,3-benzodioxol-4-ol.

12. The process of claim 1 wherein the inert organic solvent is selected from aromatic hydrocarbons, ketones, esters, ethers, and chlorinated aliphatic hydrocarbons.

13. The process of claim 1 wherein the basic catalyst is present in an amount of from 0.001 to 0.1 moles per mole of substituted phenol or naphthol.

14. The process of claim 1 wherein the molar ratio of substituted phenol or naphthol to methyl isocyanate is 1.0–1.1:1.

15. The process of claim 1 further comprising continuously feeding methyl isocyanate to the fourth reaction space, the fourth reaction space comprising a plurality of reactor vessels each reactor vessel containing a solution of the inert organic solvent, substituted phenol or naphthol and the basic catalyst.

16. The process of claim 1 further comprising continuously feeding the methyl isocyanate obtained from the second reaction space and a solution of the inert organic solvent, substituted phenol or napthol and the basic catalyst to the fourth reaction space and continuously withdrawing N-methylcarbamate from the fourth reaction space.

17. The process of claim 1 wherein the basic catalyst is selected from the tertiary amines, heterocyclic bases, alkoxides and carbonates of alkali metals or alkaline earth metals, and tin or titanium containing organic compounds.

18. The process of claim 17 wherein the basic catalyst is selected from tertiary amines and tin containing organic compounds.

* * * * *